(12) United States Patent
Sur et al.

(10) Patent No.: US 7,682,025 B2
(45) Date of Patent: Mar. 23, 2010

(54) GAZE TRACKING USING MULTIPLE IMAGES

(75) Inventors: Sudipto Sur, San Diego, CA (US); Luis M. Pestana, San Diego, CA (US)

(73) Assignee: Miralex Systems Incorporated, San Diego, CA (US)

( * ) Notice: Subject to any disclaimer, the term of this patent is extended or adjusted under 35 U.S.C. 154(b) by 0 days.

(21) Appl. No.: 12/025,716

(22) Filed: Feb. 4, 2008

(65) Prior Publication Data

US 2008/0186449 A1    Aug. 7, 2008

Related U.S. Application Data

(60) Provisional application No. 60/888,086, filed on Feb. 4, 2007.

(51) Int. Cl.
*A61B 3/14*    (2006.01)

(52) U.S. Cl. ..................... 351/209; 351/246
(58) Field of Classification Search ............ 351/209, 351/210, 211, 221, 246, 206, 205
See application file for complete search history.

(56) References Cited

U.S. PATENT DOCUMENTS 5,907,722 A * 5/1999 Suzuki ............... 396/51
2002/0181733 A1  12/2002 Peck

FOREIGN PATENT DOCUMENTS

GB     2 272 124 A     5/1994
WO    02/31581 A1     4/2002

OTHER PUBLICATIONS

PCT Notification of Transmittal of the ISR and the Written Opinion of the International Search Authority, Mailed on Jul. 2, 2008.

* cited by examiner

*Primary Examiner*—Hung X Dang
(74) *Attorney, Agent, or Firm*—Cooley Godward Kronish LLP (57) ABSTRACT

Systems and methods for facilitating gaze tracking based on multiple images are disclosed. A gaze tracking system includes an optical module configured to receive illumination from a target and provide a background and tracking channel outputs, the background channel including ambient illumination and the tracking channel including ambient and controlled added illumination at a targeted range of wavelengths. The background and tracking channel outputs are provided to an imaging module configured to provide an associated set of background and tracking images to a processor module to facilitate gaze tracking. Controlled illumination of the target may be provided by an illumination element, in conjunction with the processor module, to facilitate gaze tracking.

7 Claims, 10 Drawing Sheets

GAZE TRACKING USING MULTIPLE IMAGES

CROSS-REFERENCE TO RELATED APPLICATIONS

This application claims priority under 35 U.S.C. §119(e) to U.S. Provisional Patent Application Ser. No. 60/888,086, entitled GAZE TRACKING USING MULTIPLE IMAGES, filed on Feb. 4, 2007, to U.S. Provisional Patent Application Ser. No. 60/943,853, entitled CONTENT AND CONSUMER EVENT SEQUENCE BASED DYNAMIC AMBIENCE GENERATION, filed on Jun. 14, 2007, to U.S. Provisional Patent Application Ser. No. 60/944,097, entitled PLATFORM AND METHOD FOR CLOSED-LOOP CONTROL OF ILLUMINATION FOR GAZE TRACKING APPLICATIONS, filed on Jun. 15, 2007, to U.S. Provisional Patent Application Ser. No. 60/952,861, entitled PRODUCTIZATION APPROACHES FOR GAZE TRACKING DEVICES, filed on Jul. 30, 2007, to U.S. Provisional Patent Application Ser. No. 60/953,679, entitled OPTIMIZATION OF IMAGES SENSORS FOR USE IN GAZE TRACKING APPLICATIONS, filed on Aug. 2, 2007, to U.S. Provisional Patent Application Ser. No. 60/955,639, entitled APPLICATIONS BASED ON GAZE TRACKING INTEGRATED WITH OTHER SENSORS, ACTUATORS AND ACTIVE ELEMENTS, filed on Aug. 14, 2007, to U.S. Provisional Patent Application Ser. No. 60/957,164, entitled SYNCHRONIZATION OF IMAGE SENSOR ELEMENT EXPOSURE AND ILLUMINATION FOR GAZE TRACKING APPLICATIONS, filed on Aug. 21, 2007 and to U.S. Provisional Patent Application Ser. No. 61/021,945 entitled APPARATUS AND METHODS FOR SPATIAL REGISTRATION OF USER FEATURES IN GAZE TRACKING APPLICATIONS, filed Jan. 18, 2008. The contents of each of these applications is hereby incorporated by reference herein in its entirety for all purposes.

BACKGROUND

In many applications it is desirable to track the movement of an object such as a person's eyes to determine where the person is looking. For example, it may be desirable to track eye movement of a computer user to determine where on the computer screen the user is looking. Eye tracking can be used to provide information to a computer or other device about an area of a display the person is viewing, potentially replacing other user interface devices such as mice or trackballs, and can also be used for a wide range of other applications.

Systems for tracking eye movement, also known as eye-gazing trackers, are known in art. For example, U.S. Pat. No. 6,959,102, incorporated by reference herein, describes a single video camera based system for eye gaze tracking in the presence of ambient light, such as sunlight.

There are, however, a number of problems with current gaze tracking systems. These include compensating for variations in ambient light, variations in user aspect presented to the system, target distance from the system, system cost, as well as other problems.

Accordingly, there is a need in the art for improved gaze tracking systems and methods to address the above and other problems.

SUMMARY

The present invention is related generally to tracking applications, and in particular to systems and methods of gaze tracking associated with eyes or similar targets, wherein a set of images is provided to facilitate gaze tracking.

In one aspect the invention relates to a gaze tracking system and method including an optical element configured to receive illumination from a tracking target and process the illumination to provide an ambient component and an ambient plus lambda component, wherein the lambda component includes illumination at a targeted wavelength, targeted wavelength range, or targeted set of wavelengths to illuminate non-contiguous wavelength ranges.

In another aspect the invention relates to a gaze tracking system and method including an imaging element configured to receive illumination from a gaze tracking target and provide one or more sets of images including an ambient component and an ambient plus lambda component, wherein the lambda component includes illumination at a targeted set of wavelengths, said images further provided to a processor component to facilitate gaze tracking.

In another aspect the invention relates to a gaze tracking system and method including an illumination element configured to provide selected illumination at a targeted set of wavelengths to facilitate gaze tracking.

In another aspect the invention relates to a system and method of providing a set of images to facilitate gaze tracking including providing controlled illumination to a gaze tracking target, receiving illumination from the tracking target, separating the illumination into an ambient and ambient plus lambda component, and providing a set of images representative of the ambient and ambient plus lambda components to a processor system to facilitate tracking.

Additional aspects of the present invention are further described and illustrated herein with respect to the detailed description and drawings.

BRIEF DESCRIPTION OF THE DRAWINGS

For a better understanding of the nature of the features of the invention, reference should be made to the following detailed description taken in conjunction with the accompanying drawings, in which.

DETAILED DESCRIPTION OF EMBODIMENTS OF THE INVENTION

This application is related to U.S. Provisional Patent Application Ser. No. 60/888,086, entitled GAZE TRACKING USING MULTIPLE IMAGES, to U.S. Provisional Patent Application Ser. No. 60/943,853, entitled CONTENT AND CONSUMER EVENT SEQUENCE BASED DYNAMIC AMBIENCE GENERATION, to U.S. Provisional Patent Application Ser. No. 60/944,097, entitled PLATFORM AND METHOD FOR CLOSED-LOOP CONTROL OF ILLUMINATION FOR GAZE TRACKING APPLICATIONS, U.S. Provisional Patent Application Ser. No. 60/952,861, entitled PRODUCTIZATION APPROACHES FOR GAZE TRACKING DEVICES, to U.S. Provisional Patent Application Ser. No. 60/953,679, entitled OPTIMIZATION OF IMAGES SENSORS FOR USE IN GAZE TRACKING APPLICATIONS, to U.S. Provisional Patent Application Ser. No. 60/955,639, entitled APPLICATIONS BASED ON GAZE TRACKING INTEGRATED WITH OTHER SENSORS, ACTUATORS AND ACTIVE ELEMENTS, to U.S. Provisional Patent Application Ser. No. 60/957,164, entitled SYNCHRONIZATION OF IMAGE SENSOR ELEMENT EXPOSURE AND ILLUMINATION FOR GAZE TRACKING APPLICATIONS and to U.S. Provisional Patent Application Ser. No. 61/021,945 entitled APPARATUS AND METHODS FOR SPATIAL REGISTRATION OF USER FEATURES IN GAZE TRACKING APPLICATIONS. The contents of each of these applications is hereby incorporated by reference herein in its entirety for all purposes. These applications may be denoted collectively herein as the "related applications" for purposes of brevity.

The present invention generally relates to systems and methods for gaze tracking. As used herein gaze tracking generally describes tracking of the eye of a human or other animal, however, the systems and methods described herein may also relate to similar applications such as tracking movement of other body parts as well as objects having similar characteristics. While the embodiments herein are typically described in terms of eye tracking, it is apparent to one of skill in the art that the systems and methods described herein are applicable to other tracking applications. Accordingly, the embodiments described herein are provided for purposes of illustration, not limitation. Various embodiments of the invention are described in detail below with reference to the figures, wherein like elements are referenced with like numerals throughout unless noted otherwise.

In one aspect the invention relates to a gaze tracking system and method including an optical element configured to receive illumination from a tracking target and process the illumination to provide an ambient component and an ambient plus lambda component, wherein the lambda component includes illumination at a targeted wavelength, range of wavelengths, or set of wavelengths to accommodate non-contiguous illumination.

In another aspect the invention relates to a gaze tracking system and method including an imaging element configured to receive illumination from a gaze tracking target and provide one or more sets of images including an ambient component and an ambient plus lambda component, wherein the lambda component includes illumination at a targeted set of wavelengths, said images further provided to a processor component to facilitate gaze tracking.

In another aspect the invention relates to a gaze tracking system and method including an illumination element configured to provide selected illumination at a targeted set of wavelengths to facilitate gaze tracking.

In another aspect the invention relates to a system and method of providing a set of images to facilitate gaze tracking including providing controlled illumination to a gaze tracking target, receiving illumination from the tracking target, separating the illumination into an ambient and ambient plus lambda component, and providing a set of images representative of the ambient and ambient plus lambda components to a processor system to facilitate tracking.

Additional aspects of the present invention are further described and illustrated herein with respect to the detailed description and drawings.

Overview

Gaze tracking techniques related to tracking eye movement have been known in the art (see, e.g., Peck, U.S. Pat. No. 6,959,102, Method for Increasing the Signal-to-Noise in IR-Based Eye Gaze Trackers). These systems typically involve a camera for capturing images/video of the eyes, an optional IR illumination source, and a processing system for processing the captured images. It is well known that the eye may respond differently to illumination from visible wavelengths as compared to infra-red. For example, the bright eye effect, exemplified by glowing red pupils in flash photographs, has been used in eye tracking applications based on the ease in detecting the effect in the infra-red. Typical systems such as these focus on tracking features at the rear of the eye such as the retina.

However, current approaches are problematic in conditions where ambient sunlight is present, such as in sunlit rooms, windowed public spaces, and outdoors, where ambient infra-red illumination is relatively high. For example, potential eye damage is a concern under these conditions due to the high level of infrared illumination required to overcome the ambient lighting conditions. Peck addresses this concern by attempting to improve image signal to noise ratio by assuming that the ambient lighting does not change substantially between successive images (typically at 30 frames/second). Based on this assumption, Peck toggles IR illumination on and off between successive frames and then subtracts the ambient only illuminated frame from the previous or next ambient+infrared illuminated frame.

While the Peck approach of capturing successive illuminated and ambient only frames may provide advantages under certain conditions, it assumes that conditions do not change frame to frame, thereby failing to account for more rapidly changing lighting conditions, rapid user and/or eye movement, or other changes such as background movement and the like, and the processing includes only subtraction of successive images.

In various aspects, the present invention addresses these and other problems by providing an enhanced approach to gaze tracking which may be particularly advantageous under conditions of non-uniform and varying ambient lighting, varying aspects presented by the user to the gaze tracking system, varying distances between the user and gaze tracking system, and other potentially problematic conditions.

In one aspect, the present invention relates to capture and processing of multiple images along with knowledge and/or determination of conditions and parameters associated with the image capture. This approach can provide more robust and accurate determination of the subject's gaze direction and point of interest.

In several described embodiments, multiple images may be acquired simultaneously, providing potential performance enhancements related to speed and accuracy of processing. Moreover, if two or more images are acquired from different perspectives, such as by using two or more offset lenses/cameras, additional information about depth may be determined using 3-D techniques such as those associated with stereoscopic imaging. This approach may provide particular advantages in enhancing the fiducials that may be used to reconstruct the gaze direction.

If simultaneous acquisition approaches are used, associated mathematic operations can be performed in parallel, potentially allowing faster or more precise performance in a given time frame. Conversely, serial processing may be used if processor capability is limited or based on other constraints, such as cost. Flexibility in the chosen approach may be used to trade-off cost versus performance, allowing for construction of devices having varying cost/performance price points.

Due to the enhanced robustness of the present invention, embodiments may be implemented that allow for non-intrusive (remote) gaze detection, potentially allowing the associated system to be fully or partially unattached to the subject. For example, in some present implementations one or more cameras are attached to the head of the subject and aimed, at close range, at the subject's eyes. This can prove highly distracting as well as being physically uncomfortable. In addition, in accordance with aspects of the present invention, gaze tracking based on targets on the front of the eye surface, such as glints or pupil openings, may provide enhancements over rear eye (i.e. retinal) tracking.

In some embodiments, aspects of the present invention can be realized in small form-factor implementations. In addition, some embodiments can be implemented with low-cost, commonly available components.

Representative Applications

Embodiments of the present invention can be applied to a wide range of tracking applications. Some representative examples are further described below.

Computer Interface Devices—As mentioned previously, gaze tracking may be used for computer interface devices to determine the area of a computer screen or other display where the subject is looking. One example of such an application is a "gaze-based computer mouse," wherein a gaze tracking system is used in place of, or in conjunction with, a standard mouse. A gaze-based mouse can enhance computer use for typical users, and may enable computer use for others who are unable to use traditional I/O devices. Moreover, use of computer interfaces can be extended to non-human subjects, such as other animals, who could readily be trained to use such devices. Additional gaze based features could also be provided, such as eye-based clicking/icon selection.

Determining/Monitoring Subject Interest and Attentiveness—Gaze tracking may be useful in application requiring attentiveness, such as driving a vehicle. For example, degree of alertness, attention and/or impairment may be determined in conjunction with gaze tracking and monitoring (such as by applying a horizontal nystagmus test). Moreover, gaze tracking can also be used to implement full or partial vehicle control in some applications, thereby removing the need for physical manipulation of traditional control mechanisms. In addition, in some applications determination of a subject's field of interest may be useful and may provide additional information when combined with other audible, tactile, and/or visual cues.

Communication Devices—Gaze tracking systems can be used for a wide variety of communication devices based on the wide range of expressions that can be performed by or in conjunction with the eyes. Applications include local or remote communication, night vision and 3D navigation.

Physical and Psychological Measurement and/or Testing—Gaze tracking systems can be used as a means of non-intrusive measurement and/or testing for medical symptoms and conditions that are either physical or psychological, such as, for example, Autism Spectrum Disorder (ASD). In addition, gaze tracking can be used as a research tool in medical applications, with stored and/or real time tracking data used to correlate visual performance with other measured characteristics and/or medical conditions.

Therapies for and Amelioration of Medical Conditions—Gaze tracking may be used to provide therapy for conditions like autism, by, for example, teaching and/or reinforcing appropriate responses in certain situations. In some other conditions, for example, macular degeneration, gaze tracking can be used to ameliorate the effect of the condition or provide some relief to the subject.

Marketing Applications—Gaze tracking systems can be used for marketing analysis and associated applications. For example, gaze tracking can be used as a non-intrusive way of determining optimal placement of marketing material on various media such as print media, web pages, video, motion pictures and other types of visual media, as well as for determining and analyzing viewer interest of particular media and its associated placement. In dynamic and interactive media, gaze tracking can be used as a feedback mechanism for the control of events in the media content.

Entertainment Applications—Gaze tracking can be used to enhance interactivity with electronic and/or computer based entertainment applications such as video games and interactive programs, DVDs and the like.

Description of Embodiments

Figure 1:
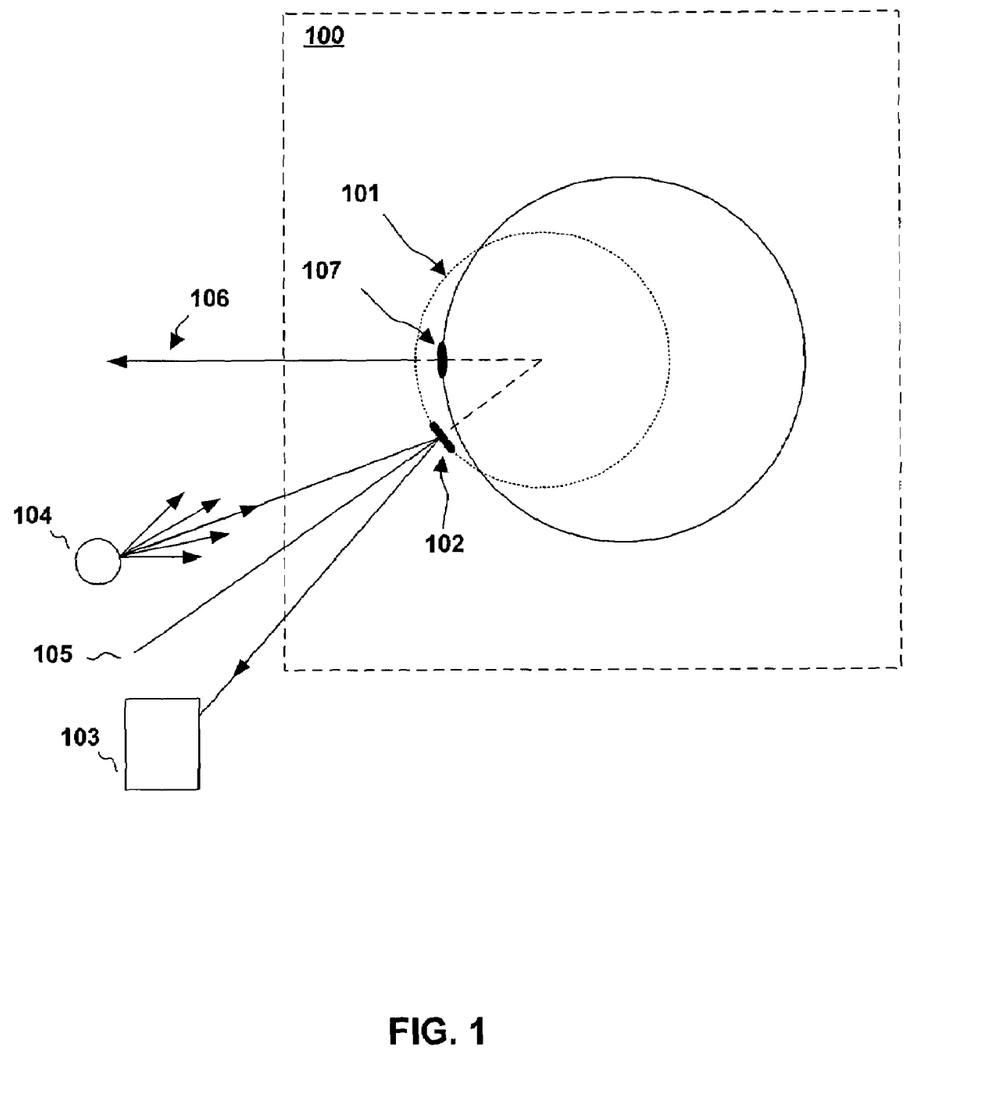
FIG. 1 illustrates a tracking target such as an eye, as well as the relevant tracking fiducials such as a glint and/or pupil mass center.

FIG. 1 is a block diagram illustrating a simplified side view of the human eye 100 as a representative gaze-tracking target. The corneal bulge 101 behaves like a convex mirror which may be approximated by a sphere with a radius of ~7.8 mm (See, e.g., Forrester et al., The Eye: Basic Sciences in Practice, 2001). The corneal reflection or glint 102 is detected by the imager 103 as a virtual image of the illumination source 104. Additional details of embodiments of systems and methods for implementing this detection are described and illustrated with respect to the following figures. The bisector 105 of the angle formed by the illumination source and the imager may be extended to the center of the corneal sphere. A vector from the corneal sphere center 106 extended through the pupil center 107 will yield the direction of the user's point of regard for gaze tracking applications.

Figure 2:
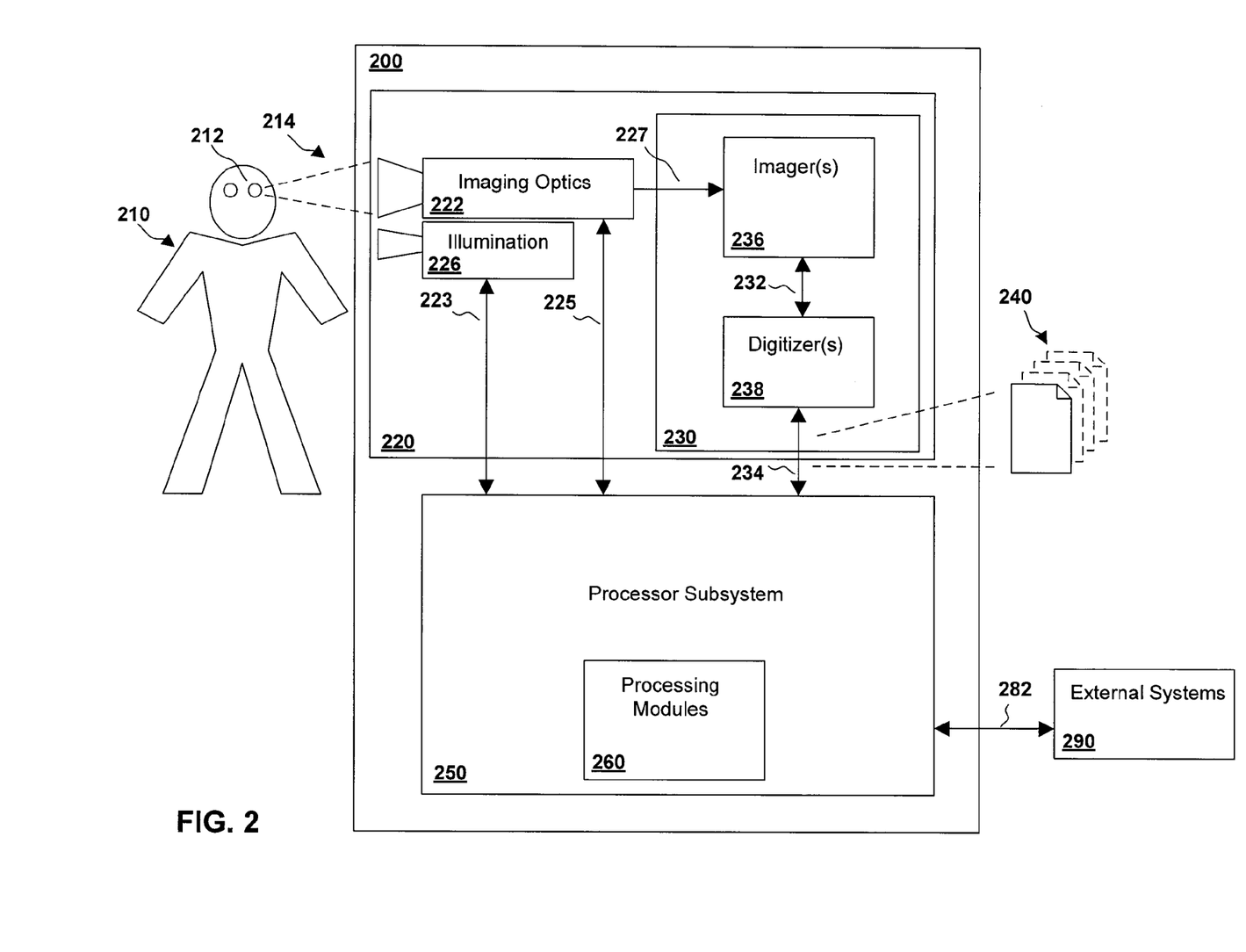
FIG. 2 illustrates a gaze tracking system for facilitating embodiments of the present invention.

Attention is now directed to FIG. 2 which illustrates a system 200 configured to facilitate one or more embodiments of the present invention. A system 200 will generally include an imaging subsystem 220 and a processor subsystem 250, with imaging subsystem 220 further including imaging optics elements, optical conversion elements, and optional illumination elements. In operation, a subject 210 is positioned relative to image optics subsystem 222 so that a target or fiducial 212 associated with a subject, such as one or both subject eyes, may be identified and optically tracked by system 200. In an exemplary embodiment, fiducial 212 will be associated with a glint or image reflection from the surface of the eye, pupil, or other feature associated with the tracked object, such as is illustrated in FIG. 1.

Imaging optics subsystem 222 may include optical elements such as lenses and lens assemblies, filters, mechanical controls, switches, motor drives, shutters and the like to provide optical output through channel 227 to optical conversion subsystem 230. The optical elements may comprise a single lens assembly and associated imaging elements for capture of a single image at a time, or may include multiple lens assemblies and/or associated imaging elements for simultaneous capture of two or more images. Imaging optics subsystem 222 may also include one or more illumination elements 226 to providing illumination on subject 210 at a fixed wavelength or combination or range of wavelengths in order to enhance image tracking performance by providing selective illumination to subject 210. In a typical embodiment illumination element 226 will provide controlled illumination at infra-red wavelengths, however, in some embodiments other wavelengths selected to provide added illumination over ambient may be used. The output of illumination element 226 may be dynamically adjusted based on feedback information such as information obtained from previous images, ambient lighting levels and changes in ambient light, subject and/or background positions and/or velocities of motion and/or other parameters. The output from illumination element 226 may be provided in a switched and/or controlled amplitude mode, and may be synchronized with image acquisition stages and/or algorithm processing stages as performed in processor subsystem 250 and implemented in one or more processing modules 260.

The optical output from subsystem 222 may then be provided to an image conversion subsystem 230, through channel 227, for conversion from optical to electronic form. Typically, image conversion subsystem 230 will include one or more imagers 236 configured to receive one or more optical images from subsystem 220 and convert them to an electronic signal. Image sensing elements in imagers 236 may be charge coupled devices (CCDs), complimentary metal oxide semiconductor (CMOS) devices, or other devices capable of capturing images in electronic form. The electronic signal representing the one or more images may then be transferred from imagers 236 through channel 232 to one or more digitizers 238 configured to convert the imager output into a digitized form. In an exemplary embodiment, the output from digitizers 238 comprises a series of image frames 240 as shown in FIG. 2. These images may be single image frames, serial or parallel image frames (based on two or more different illumination profiles), and/or composite image frames including two or more images on each frame and/or based on two or more target or camera positions.

The image frames 240 may then be provided to processor subsystem 250 through channel 234 where they may be processed by one or more processing modules (which may be implemented in a variety of modalities such as, for example, hardware, firmware, software and/or programmable devices such as FPGAs) 260 to track movement of the target, such as eye movements, and generate corresponding output signals or output data. The tracking output information may be used directly by processor subsystem 250, such as in embodiments where the processor subsystem is part of a larger computer system including peripherals such as keyboards, mice, other user interfaces, displays and other peripherals and outputs. Alternately and/or in addition, the output of processing module 260 may be provided to one or more external systems 290, such as an external computer system or network, monitoring system, control system or other type of external system or device. Additionally, the processing may be controlled or changed by commands which are communicated through the communication channel 282 by the external system 290. In some embodiments some or all of the processing functionality provided by software modules 260 may be implemented on one or more external systems 290.

Processor subsystem 250 will typically include a combination of hardware such as digital processors, processor readable memories, mass storage such as hard drives or other mass storage elements, input and output interfaces such as keyboards, mice, displays and the like, as well as one or more communication channels/interfaces 282 such as serial or parallel port interfaces, USB, Firewire, Ethernet, Wireless (e.g. 802.11, Wi-Fi) or other interfaces supporting communication to one or more external systems 290.

Processor subsystem 250 will also typically include one or more processing modules 260 configured to perform functions related to system control, communication as well as image processing. In a typical embodiment processing module 260 will provide software based control and/or power control signals for illumination element 226 as well as for optical elements included in system 220 such as shutters, focusing elements, mechanical elements, filters, triggers and the like. For example, processing module 260 may also include one or more modules to provide control signals for imaging optics 222 via channel 225 and/or to illumination element 226 via channel 223.

Signal processing functions associated with processing module 260 may include image processing on image frames 240 to generate tracking related data and output. These may consist of operations on individual pixels, pixel subsets, individual images, image sets, and/or operations on temporal sequences and/or simultaneously captured images, along with associated analytical functions, to determine the gaze direction of the target from such processing. It is noted that in some embodiments some or all of the signal processing and/or control functionality associated with module or modules 260 may be implemented in one or more external systems 290.

Figure 3:
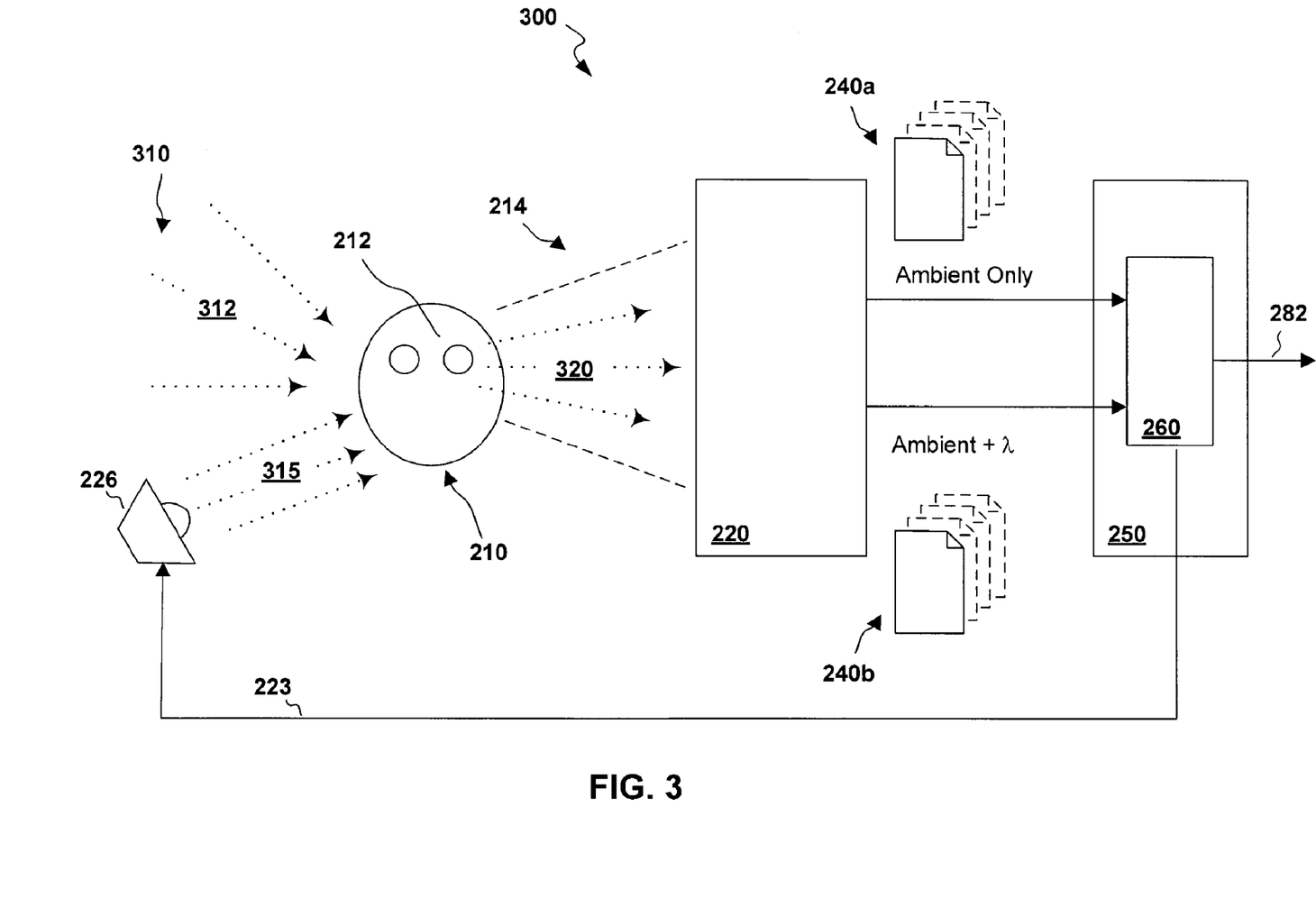
FIG. 3 illustrates a generalized system for facilitating gaze tracking applications in accordance with aspects of the present invention.

Attention is now directed to FIG. 3 which illustrates a generalized view of a system in accordance with aspects of the present invention. As shown in FIG. 3, a system 300 may be configured to receive illumination 320 from a subject 210. For purposes of brevity, illumination may also be referred to herein as "light." While the term light typically refers to visible light, as used herein it may also include other wavelengths of electromagnetic radiation such as in the ultraviolet, infra-red, X-ray or other electromagnetic radiation bands.

Illumination 320 may include ambient illumination 312, including incident ambient light along with ambient light reflected from subject 210, as well as, in typical embodiments, additional illumination at a selected wavelength, range of wavelengths or set of wavelengths 315 (these selected or targeted wavelengths may also be denoted herein for brevity as lambda or by the symbol "$\lambda$"). Alternately, in some embodiments illumination 315 ($\lambda$) may be a wavelength, range of wavelengths, or set of wavelengths included within the incident ambient light 310. In either case, the light incident to imaging subsystem 220 will typically include an ambient light component and a targeted light ($\lambda$) component. A reference fiducial 212, such as an eye or glint on an eye of subject 210, is selected for tracking by system 200.

Illumination element 226 is typically configured to provide controlled illumination 315 to subject 210. The illumination may be switched on or off, and/or may have the wavelength(s) and/or intensity controlled. This is typically done through a signal or direct power provided through channel 223 from processor subsystem 250, based on control signals as generated in one or more of processing modules 260. Illumination control may be coordinated with associated image acquisition and processing as is further described below to selectively enable or disable illumination 315. In some embodiments, illumination control will be provided by a feedback control system based in part on measurements of light conditions and/or previous images. Determination is typically done based at least in part on conditions captured on or in connection with images 240, however, in some embodiments a separate subsystem (not shown) may be provided to provide a separate input related to detected lighting conditions.

Figure 6:
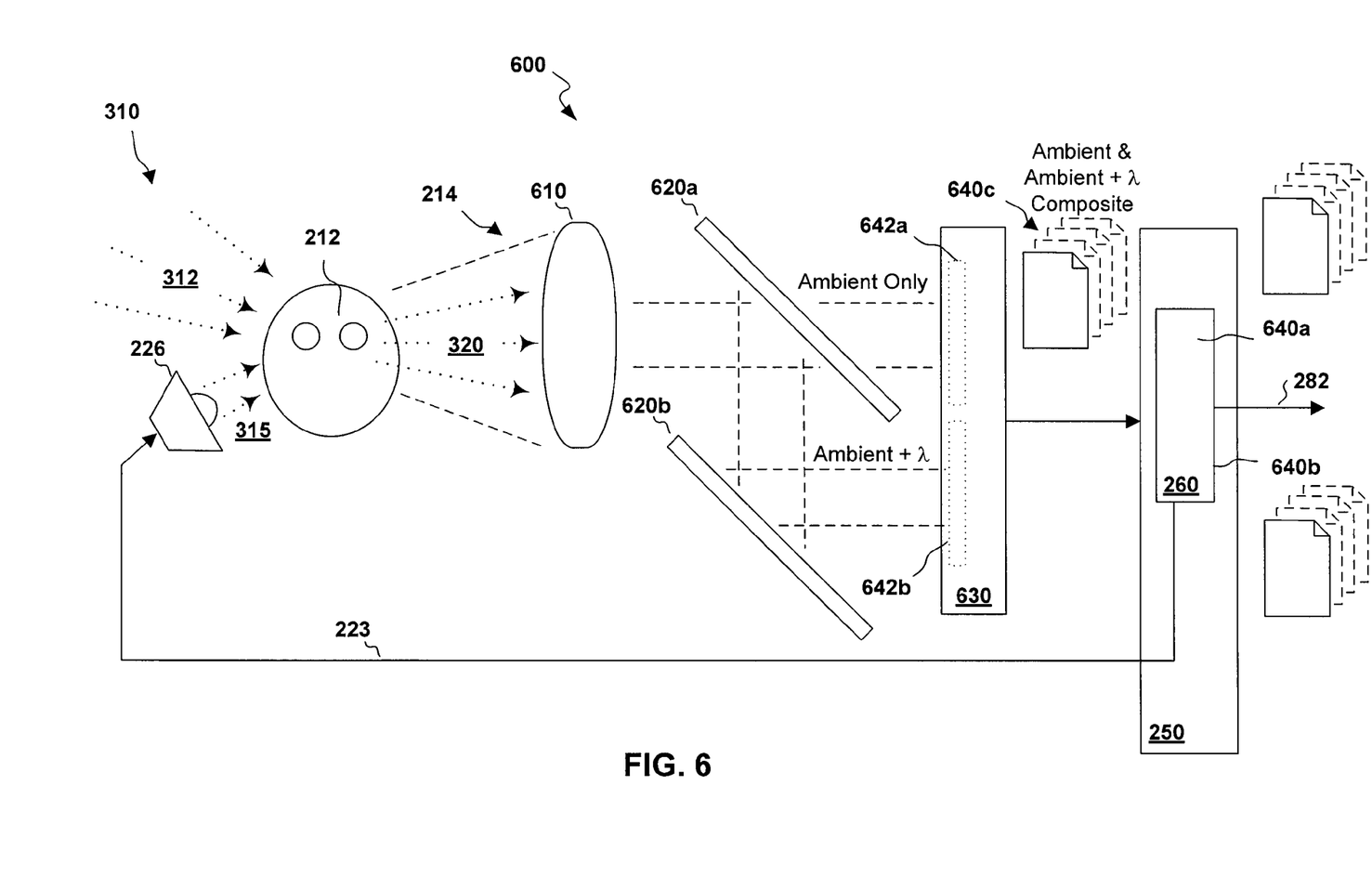
FIG. 6 illustrates one embodiment of a gaze tracking system in accordance with aspects of the present invention.

In operation, imaging subsystem 220 receives incoming illumination 320 and then processes the incoming light to provide a set of digitized images 240 (typically in the form of a digitized image file such as may be provided in a standard image file format or as an in-memory representation of the image or images) including a set of ambient only images 240*a* and a set of ambient plus λ images 240*b*. In some embodiments images 240*a* and 240*b* are separate images, whereas in other embodiments a set of composite images 640*c* (such as are shown in FIG. 6) may be provided. Images 240 are then provided to processor subsystem 250 where they may be processed in one or more processing modules 260 to generate, store, utilize for further analysis (e.g. for feedback to a control system) and/or communicate gaze tracking information, as well as, in some embodiments, to output data, images, and/or gaze tracking information to external systems 290 via channel 282.

Figure 4:
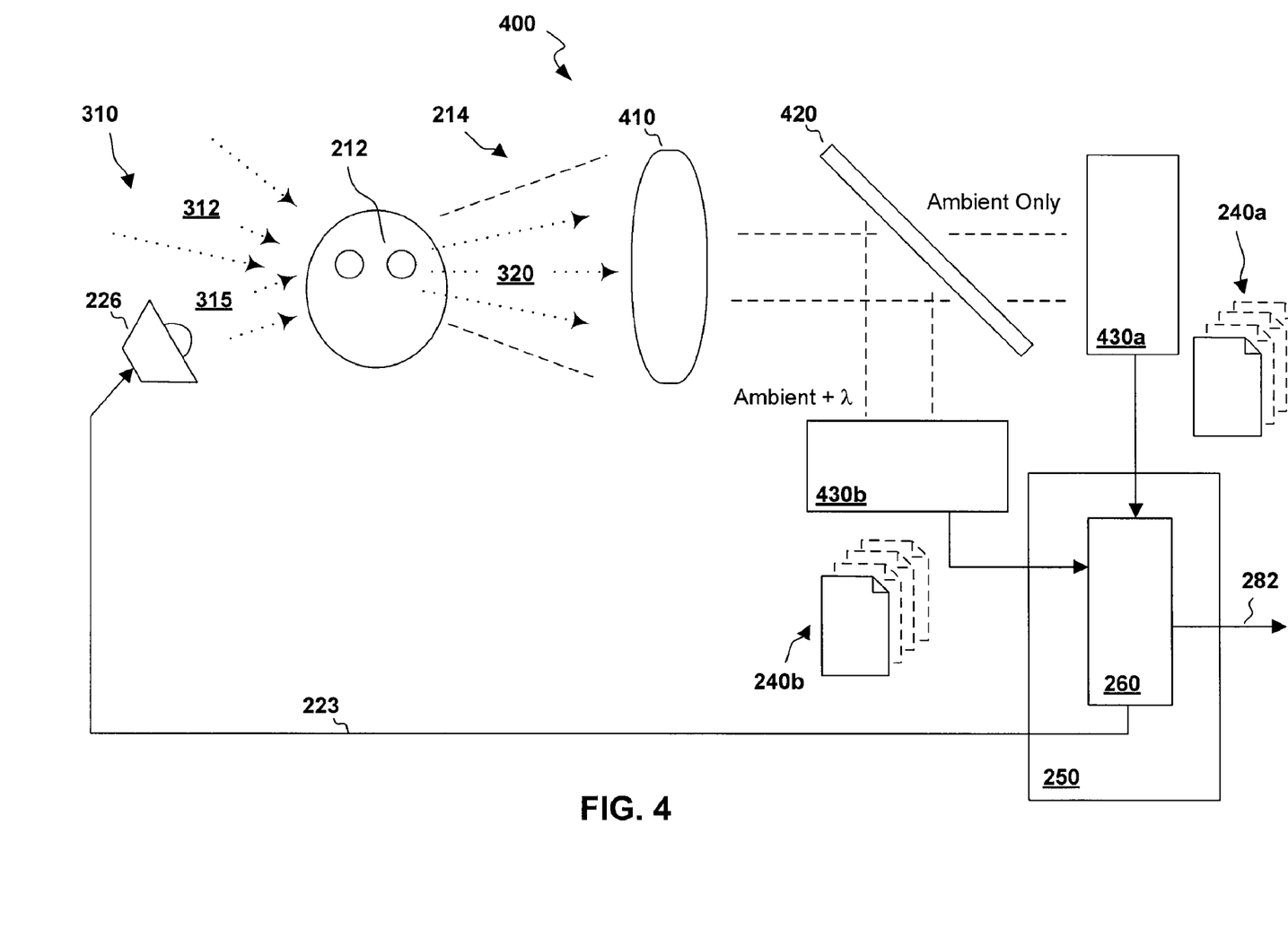
FIG. 4 illustrates one embodiment of a gaze tracking system in accordance with aspects of the present invention.

Attention is now directed to FIG. 4 which illustrates additional details of one embodiment of a single lens/imaging element gaze tracking system 400 in accordance with aspects of the present invention. As shown in FIG. 4, divergent illumination 320 may be provided to single lens element 410 which then directs the light to an optical element for separation of the illumination into an ambient only component (also denoted as the "background" channel) and an ambient+λ component (also denoted as the "tracking" channel). It is noted that lens element 410 is typically a lens assembly rather a single lens, with the lens assembly including or more lens elements, mounting elements, optional filters, along with any other associated control, mechanical and/or other components.

A dichroic mirror 420 may be used to effect the separation of ambient and ambient+λ components. As shown in FIG. 4, the dichroic mirror 420 functions as an optical filter with the ambient only component directed to image conversion subsystem 430*a*, where the incoming background channel component is then imaged and digitized to produce a set of images 240*a* representing the target as illuminated solely by the ambient component. In addition, dichroic mirror 420 may act as a reflector to provide the ambient+λ component to a second image conversion subsystem 430*b*, which likewise images and digitizes the tracking channel component to produce a set of images 240*b*. Image conversion subsystems 430*a* and 430*b* are typically elements of image conversion subsystem 230 as shown in FIG. 2. In some embodiments imaging sensors or sensing elements associated with subsystems 430*a* and 430*b* may be configured to be sensitive to a common range of wavelengths, however, in other embodiments background and tracking channel imaging sensors may each be configured to be sensitive to particular wavelengths of the background and tracking channels respectively. Images associated with the background and tracking channels may be acquired simultaneously or may be time delayed with respect to each other, wherein the time delay between acquisition may be dynamically set by the tracking algorithm used by processing module 260.

Image sets 240*a* and 240*b* may then be provided to processor subsystem 250 for processing in processing modules 260 to gaze track target 212. The output tracking information may then be used for tracking related functions in processor subsystem 250 and/or may be provided to one or more external devices via channel 282.

Processing module 260 may generate an illumination control signal or power signal that may be provided to illumination element 226 through channel 223 to synchronize illumination 315 with image acquisition at image conversion subsystems 430*a* and 430*b*. In some embodiments, illumination control may be done by programmatically setting the tracking channel illumination level (via software, firmware, and/or hardware) based in whole or in part on image information obtained from a previous frame such as a previous background channel frame and/or based on separately acquired illumination information.

Figure 5:
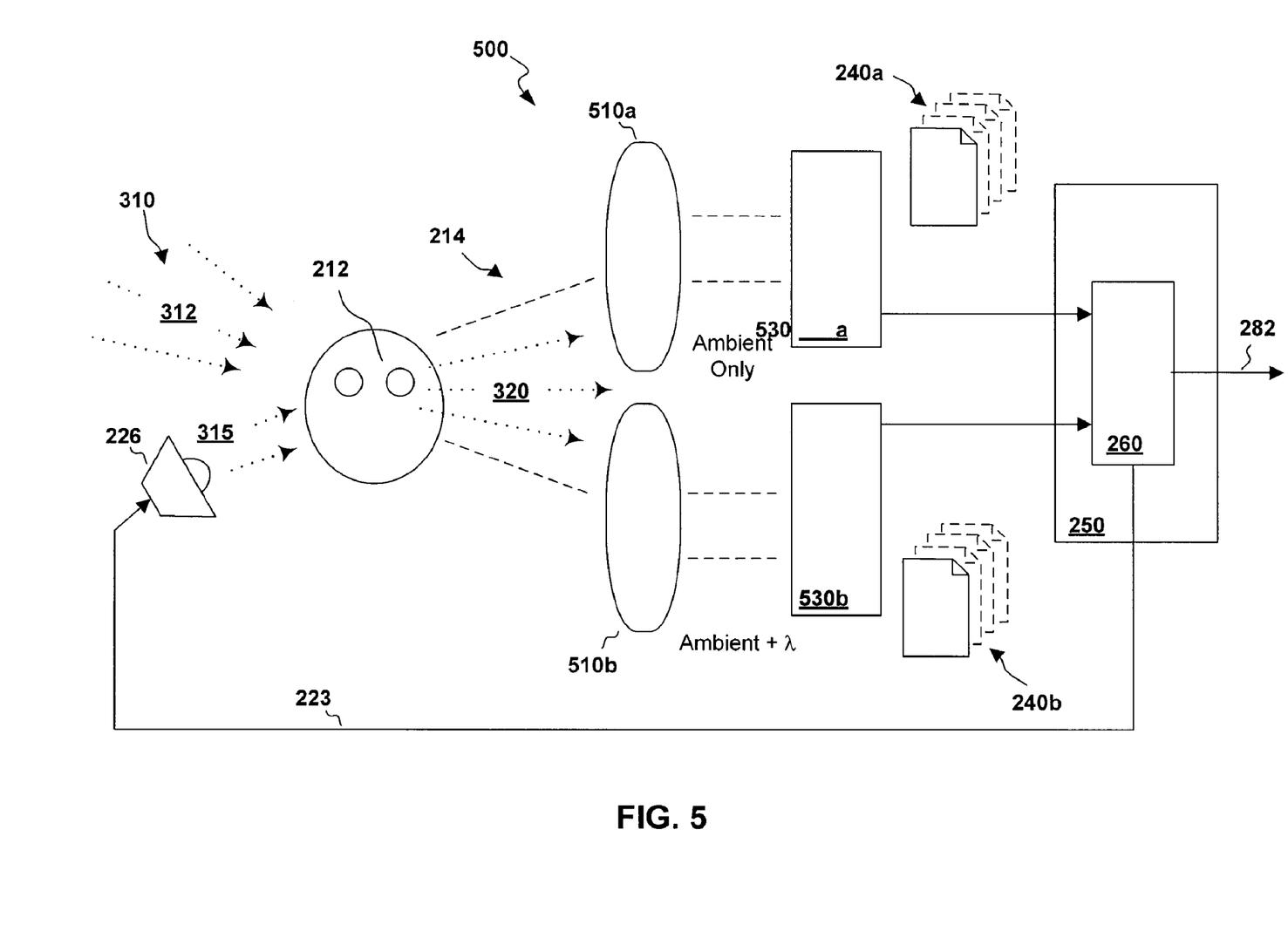
FIG. 5 illustrates one embodiment of a gaze tracking system in accordance with aspects of the present invention.

Attention is now directed to FIG. 5, which illustrates another embodiment of the present invention comprising a dual lens/imaging element gaze tracking system 500 in accordance with aspects of the present invention. While the illustrated embodiment is shown with two lens/imaging elements, it is noted that alternate embodiments within the spirit and scope of the present invention may include three or more lens/imaging elements in an analogous fashion to that shown in FIG. 5.

As shown in FIG. 5, divergent illumination 320 may be provided to two lens elements 510*a* and 510*b*, which then direct the incoming light to image conversion subsystems 530*a* and 530*b*, sensitive to the ambient only component (background channel) and ambient+λ component (tracking channel) respectively. As with element 410 as shown in FIG. 4, elements 510*a* and 510*b* are typically lens assemblies comprising one or more lenses along with associated mounting, mechanical and/or other related components. Image sets 240*a* and 240*b* associated with the background and tracking channels may then be generated by imaging elements within subsystems 530*a* and 530*b*. Image conversion subsystems 530*a* and 530*b* are typically elements of image conversion subsystem 230 as shown in FIG. 2. Likewise, as with imaging elements in subsystems 430*a* and 430*b*, imaging sensors or sensing elements in subsystems 530*a* and 530*b* may be configured to be sensitive to a common range of wavelengths, however, in other embodiments background and tracking channel imaging sensors may each be configured to be sensitive to particular wavelengths of the background and tracking channels respectively. Image sets 240*a* and 240*b* may be acquired simultaneously or may be time delayed with respect to each other, wherein the time delay between acquisitions may be dynamically set by the tracking algorithm used by Processing module 260.

Image sets 240*a* and 240*b* may then be provided to processor subsystem 250 for processing in processing modules 260, to gaze track target 212. The output tracking information may then be used for tracking related functions in processor subsystem 250 and/or may be provided to one or more external devices 290 via channel 282.

Processing module 260 may generate an illumination control signal or power signal that may be provided to illumination element 226 through channel 223 to synchronize illumination 315 with image acquisition at image conversion subsystems 530*a* and 530*b*. In some embodiments, illumination control may be done by programmatically setting the tracking channel illumination level (via software, firmware, and/or hardware) based in whole or in part on image information obtained from a previous frame such as a previous background channel frame.

FIG. 6 illustrates another embodiment of the present invention comprising a single lens/imaging element gaze tracking system 600 in accordance with aspects of the present invention. As shown in FIG. 6, divergent illumination 320 may be provided to single lens element 610, with the light then separated into ambient (background) and ambient+λ (tracking) channels. Lens element 610 is typically a lens assembly rather a single lens, with the lens assembly including or more lens elements, mounting elements, optional filters, along with any other associated control, mechanical and/or other components.

A dichroic mirror 620a may be used in conjunction with mirror 620b to direct the background and tracking channels accordingly to a single image conversion subsystem 630, subsystem 630 typically being an implementation of subsystem 230 as shown in FIG. 2. Respective background and tracking images 642a and 642b may be formed on a single image output set 640c, with each image in the set comprising a composite of the ambient and ambient+λ images. In a typical embodiment the imaging element of subsystem 630 is sensitive to both background and tracking channel wavelengths, however, corresponding filtering and/or composite imaging elements with variable sensitivity may be provided.

In an alternate embodiment, a second lens element 610 (not shown) may be provided to replace mirror 620b to provide the ambient+λ component directly to imaging subsystem 630.

Image set 640c may then be provided to processor subsystem 250 for processing in processing modules 260 to gaze track target 212. The composite image set 640c may be separated in the processor subsystem 250 into background and tracking image sets for further processing into gaze tracking information. The output tracking information may then be used for tracking related functions in processor subsystem 250 and/or may be provided to one or more external devices 290 via channel 282.

Processing module 260 may generate an illumination control signal or power signal that may be provided to illumination element 226 through channel 223 to synchronize illumination 315 with image acquisition at image conversion subsystem 630. In some embodiments, illumination control may be done by programmatically setting the tracking channel illumination level (via software, firmware, and/or hardware) based in whole or in part on image information obtained from a previous frame such as a previous background channel frame.

Figure 7:
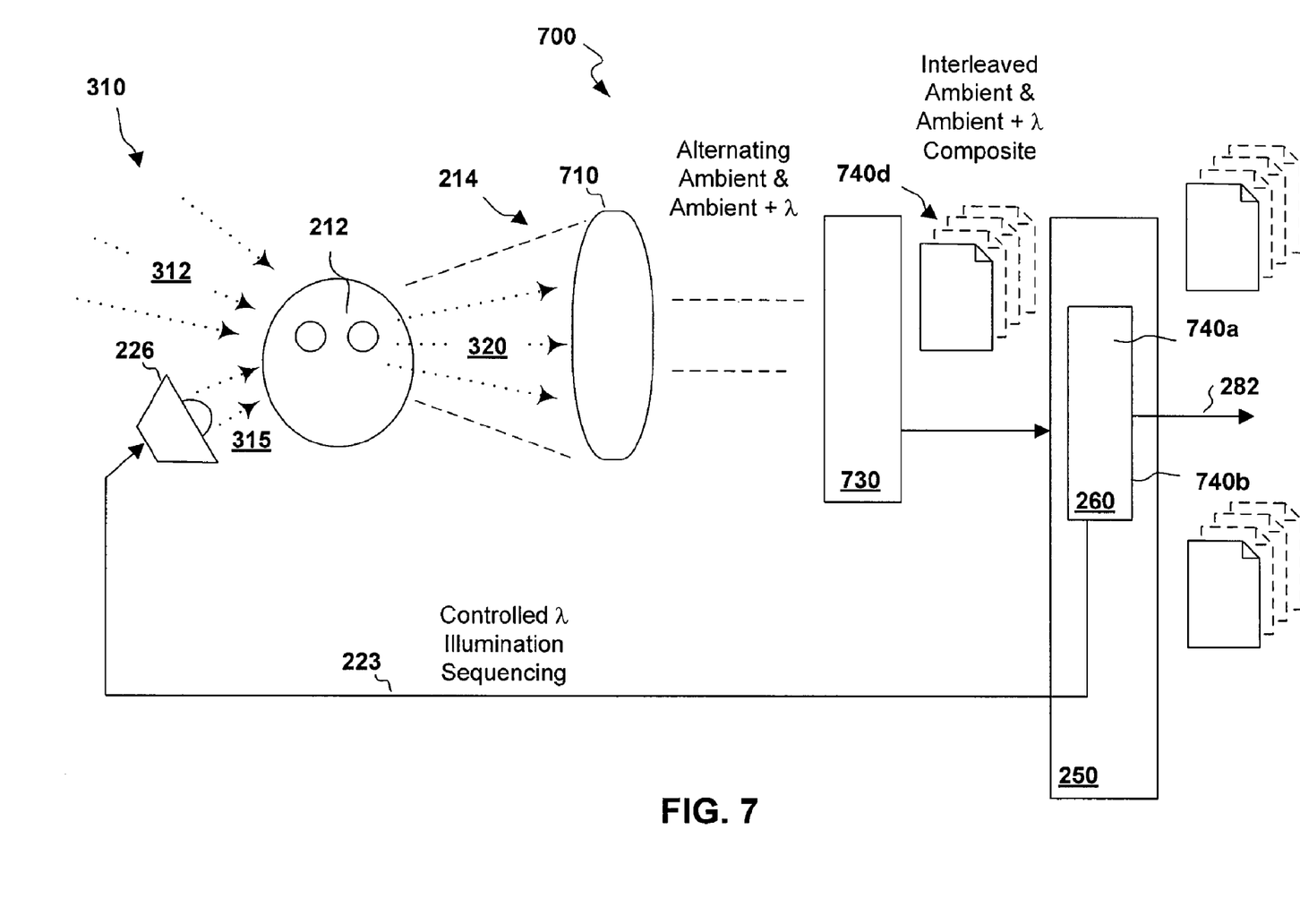
FIG. 7 illustrates one embodiment of a gaze tracking system in accordance with aspects of the present invention.

FIG. 7 illustrates yet another embodiment of the present invention comprising a single lens/imaging element gaze tracking system 700 in accordance with aspects of the present invention. As shown in FIG. 7, divergent illumination 320 may be provided to single lens element 710, with the light then separated into ambient (background) and ambient+λ (tracking) channels based on synchronized illumination using illumination element 226 under control of processing module 260. It is noted that lens element 710 is typically a lens assembly rather a single lens, with the lens assembly including one or more lens elements, mounting elements, optional filters, along with any other associated control, mechanical and/or other components.

A single image conversion subsystem 730, configured to be sensitive to both the background and tracking channel wavelengths, may be used to successively image background and tracking channel images into image set 740d. The associated illumination provided by illumination element 226 may be based on varying the illumination level for background and tracking images, toggling illumination on or off, and/or by varying the wavelength or wavelengths of illumination in successive images to provide varying illumination characteristics to successive images. Other controlled illumination sequencing may also be applied based on the image sensors, subject, subject position, imaging angle, ambient lighting as well as on other variables.

Image set 740d may then be provided to processor subsystem 250 for processing in processing modules 260 to gaze track target 212. The composite image set 740d may then be separated in the processor subsystem 250 into background and tracking image sets for further processing into tracking information. It is noted that the time delay between successive image acquisitions should be set to a value that would be small relative to the motion speed of the target or background so that time offset background and tracking images would be based on substantially the same target position. The output tracking information may then be used for tracking related functions in processor subsystem 250 and/or may be provided to one or more external devices 290 via channel 282.

In the embodiment illustrated in FIG. 7, processing module 260 generate a synchronized illumination control signal or power signal that may be provided to illumination element 226 through channel 223. This signal synchronizes illumination 315 with image acquisition at image conversion subsystem 730 so that successive images are illuminated accordingly.

It is further noted that variations on the embodiments shown in FIGS. 2-7 may be implemented, such as by providing systems having dual versions of the components shown in FIGS. 2-7 comprising multiple lens elements and associated imaging components to support stereoscopic or multiple perspective imaging. It is apparent to one of skill in the art that other permutations and combinations within the spirit and scope of the invention may also be provided.

In summary, in accordance with aspects of the present invention, systems as illustrated with respect to FIGS. 2-7 may be used to provide a set of images with different characteristics related to differences in illumination conditions. These approaches can enhance gaze tracking applications by using multiple images to accentuate features of interest in gaze tracking. In one example, a pair of simultaneously acquired images can be processed by processing related images in the image data sets, where one image is acquired under ambient conditions and the second image under ambient plus infra-red conditions or other under controlled conditions. The processed image differences can accentuate features which strongly reflect infra-red light, such as the surface of the eye and the cornea in particular. This approach may provide a localized, robust accurate depiction of the glint due to reflection of the light source on the subject's eye. This information may be very useful in determining the direction of the subject's gaze. Moreover, knowledge of some or all of the ambient conditions and acquisition parameters makes possible myriad mathematical operations using sets of images which accentuate the determination of the fiducials and their properties of interest. In some embodiments, further use of structured lighting such as may be provided by element 226 may enhance determination of related parameters such as subject distance, facial features and biological species determination. Image focus information may also be used for distance computation or for determining other subject related parameters.

Figure 8:
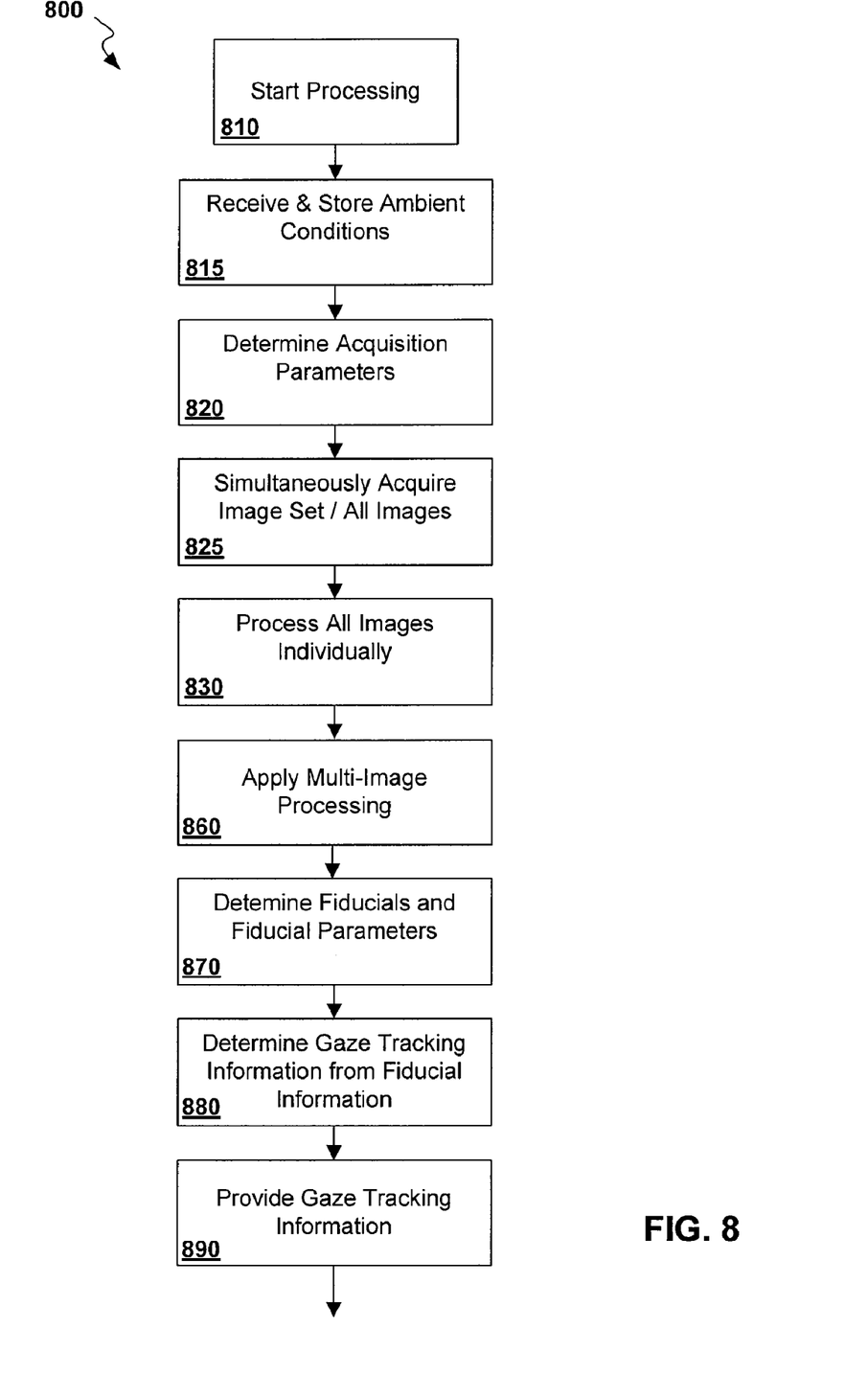
FIG. 8 illustrates one embodiment of a process for processing multiple images simultaneously in accordance with aspects of the present invention.

FIG. 8 illustrates one embodiment of a process 800 for processing multiple images to support gaze tracking in accordance with aspects of the present invention. As shown in FIG. 8, images may be acquired simultaneously, such as by systems as illustrated in the preceding figures. Processing may begin at stage 810, with information related to ambient conditions received and stored at stage 815. Acquisition parameters may be determined at stage 820 and may be used to set acquisition related variables such as illumination, optical acquisition parameters, acquisition sequencing and the like. A set of images may then be simultaneously acquired at stage 825, with the images processed individually at stage 830. Multiple image processing may then be applied at stage 860, with the fiducial and associated parameters determined at stage 870. Gaze tracking information may then be determined at stage 880 based on the fiducial information, and the gaze tracking information may then be used for additional applications and/or provided to one or more external systems at stage 890.

Figure 9A:
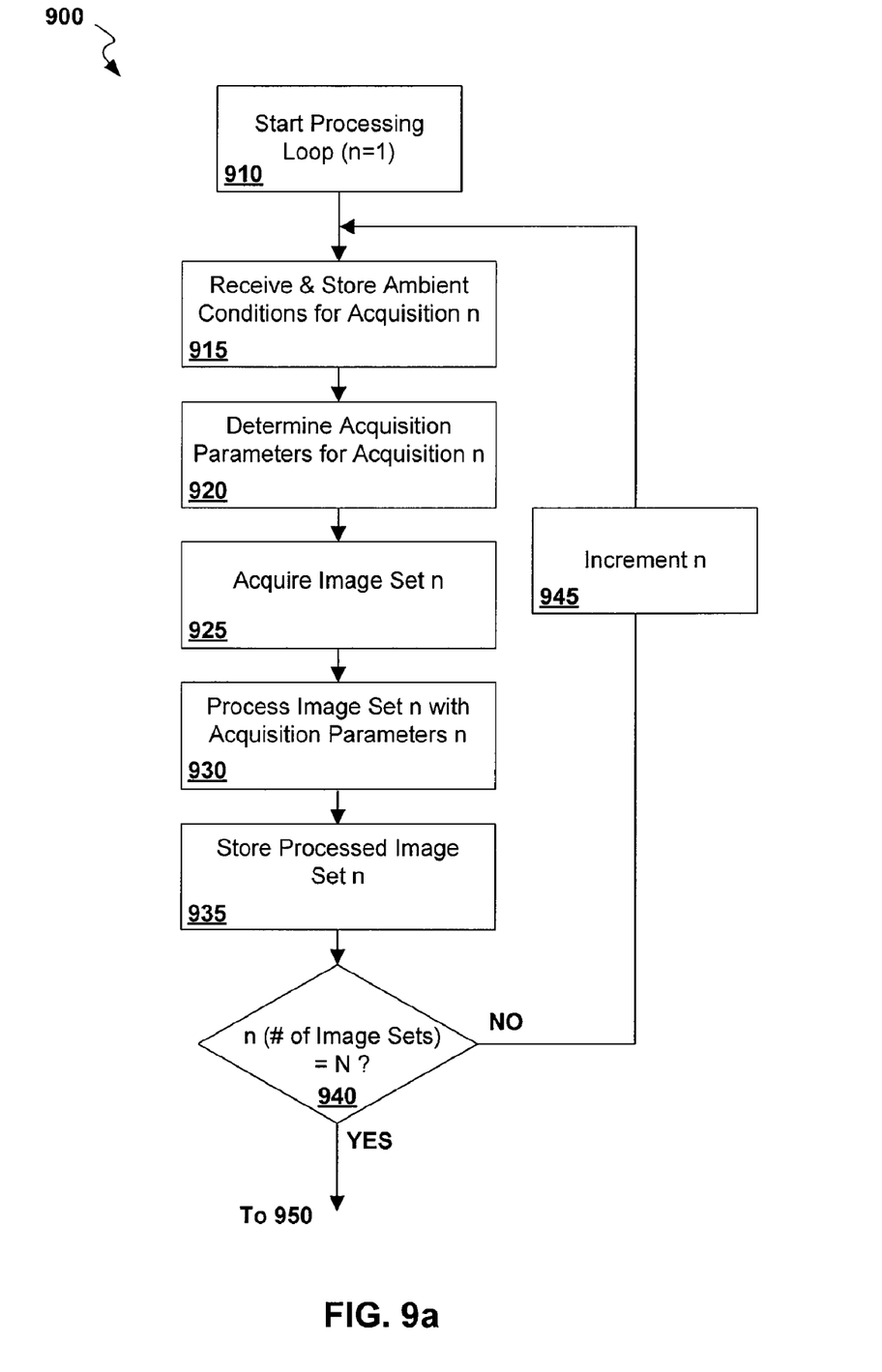
FIGS. 9a and 9b illustrate one embodiment of a process for receiving and processing multiple images sequentially in accordance with aspects of the present invention.

FIGS. 9a and 9b illustrate another embodiment of a process 900 for processing multiple images in a block of N images. Process 900 may begin as shown in FIG. 9a with a start stage 910 wherein the loop counter n is set to 1, with a total loop count of N. Ambient conditions for acquisition n of N may be received and stored at stage 915. Acquisition parameters for the acquisition may then be determined at stage 920, and may be used to set acquisition related variables such as illumination, optical acquisition parameters, acquisition sequencing and the like. An image set (comprising one or more images as described previously with respect to FIGS. 2-7) for acquisition n may then be acquired and stored at stage 925. The image set n may then be processed using associated acquisition parameters n at stage 930, and then stored at stage 935. The loop counter may be tested at stage 940 and the loop repeated if n<N, with the loop counter n incremented at stage 945.

Figure 9B:
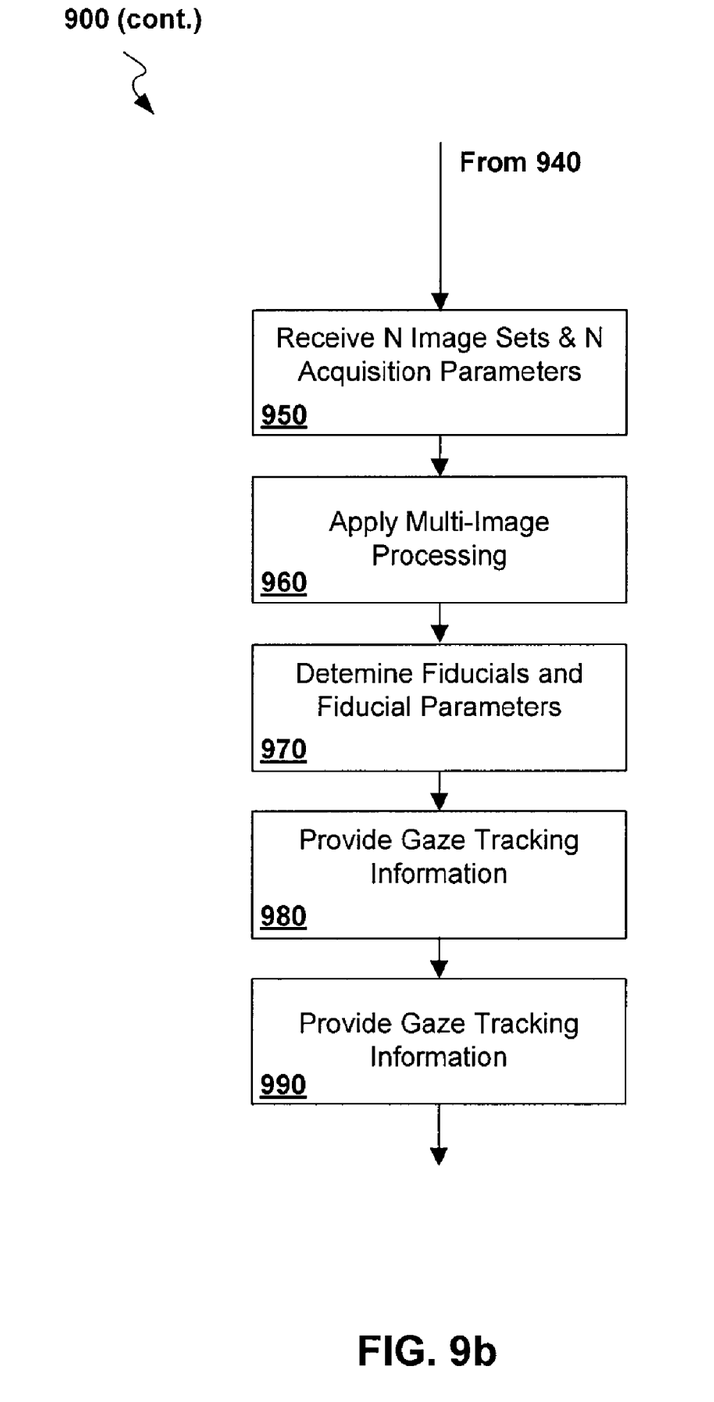

If the loop has completed at stage 940 execution may continue at stage 950 as shown in FIG. 9b, where N image sets and associated acquisition parameters may be received and stored for multi-image processing. Multi-image processing may be applied at stage 960, with fiducials and fiducial parameters determined at stage 990. Gaze tracking information may then be determined at stage 980 based on the fiducial information, and the gaze tracking information may then be used for additional applications and/or provided to one or more external systems at stage 990.

It is noted that in various embodiments the present invention may relate to processes such as are described or illustrated herein and/or in the related applications. These processes are typically implemented in one or more modules comprising systems as described herein and/or in the related applications, and such modules may include computer software stored on a computer readable medium including instructions configured to be executed by one or more processors. It is further noted that, while the processes described and illustrated herein and/or in the related applications may include particular stages, it is apparent that other processes including fewer, more, or different stages than those described and shown are also within the spirit and scope of the present invention. Accordingly, the processes shown herein and in the related applications are provided for purposes of illustration, not limitation.

Some embodiments of the present invention may include computer software and/or computer hardware/software combinations configured to implement one or more processes or functions associated with the present invention. These embodiments may be in the form of modules implementing functionality in software and/or hardware software combinations. Embodiments may also take the form of a computer storage product with a computer-readable medium having computer code thereon for performing various computer-implemented operations, such as operations related to functionality as describe herein. The media and computer code may be those specially designed and constructed for the purposes of the present invention, or they may be of the kind well known and available to those having skill in the computer software arts, or they may be a combination of both.

Examples of computer-readable media within the spirit and scope of the present invention include, but are not limited to: magnetic media such as hard disks; optical media such as CD-ROMs, DVDs and holographic devices; magneto-optical media; and hardware devices that are specially configured to store and execute program code, such as programmable microcontrollers, application-specific integrated circuits ("ASICs"), programmable logic devices ("PLDs") and ROM and RAM devices. Examples of computer code may include machine code, such as produced by a compiler, and files containing higher-level code that are executed by a computer using an interpreter. Computer code may be comprised of one or more modules executing a particular process or processes to provide useful results, and the modules may communicate with one another via means known in the art. For example, some embodiments of the invention may be implemented using assembly language, Java, C, C#, C++, or other programming languages and software development tools as are known in the art. Other embodiments of the invention may be implemented in hardwired circuitry in place of, or in combination with, machine-executable software instructions.

The foregoing description, for purposes of explanation, used specific nomenclature to provide a thorough understanding of the invention. However, it will be apparent to one skilled in the art that the specific details are not required in order to practice the invention. In other instances, well-known circuits and devices are shown in block diagram form in order to avoid unnecessary distraction from the underlying invention. Thus, the foregoing descriptions of specific embodiments of the present invention are presented for purposes of illustration and description. They are not intended to be exhaustive or to limit the invention to the precise forms disclosed; obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the following claims and their equivalents define the scope of the invention.

What is claimed is:

1. A gaze tracking system comprising:
   an optical module disposed to receive, from a target, illumination including an ambient light component and a controlled light component, and provide a background output and a tracking output, said background output consisting substantially of the ambient light component and said tracking output including the ambient light component and the controlled light component;
   an imaging module disposed to receive the tracking output and the background output and provide a set of images based on the tracking output and background output wherein the set of images provided by the imaging module include a set of background channel images based on the background output and a set of tracking channel images based on the tracking output and wherein a plurality of images of the set of background channel images and a corresponding plurality of images of the set of tracking channel images are captured simultaneously; and a processor module disposed to:
receive the set of images;
provide, based on the set of images, gaze tracking data; and
store, in a processor readable memory, the gaze tracking data.

2. A gaze tracking system comprising:
an optical module disposed to receive, from a target, illumination including an ambient light component and a controlled light component, and provide a background output and a tracking output, said background output consisting substantially of the ambient light component and said tracking output including the ambient light component and the controlled light component;
an imaging module disposed to receive the tracking output and the background output and provide a set of images based on the tracking output and background output wherein the set of images provided by the imaging module comprises a set of composite images, each composite image of the set of composite images including a background channel image and a tracking channel image wherein the tracking channel image and background channel image are captured simultaneously; and
a processor module disposed to:
receive the set of images;
provide, based on the set of images, gaze tracking data; and
store, in a processor readable memory, the gaze tracking data.

3. A gaze tracking system comprising:
an optical module disposed to receive, from a target, illumination including an ambient light component and a controlled light component, and provide a background output and a tracking output, said background output consisting substantially of the ambient light component and said tracking output including the ambient light component and the controlled light component, wherein the optical module comprises:
  a lens assembly;
  a filter assembly disposed to generate the background output and tracking output, said filter assembly including a dichroic mirror configured to provide the background output and a second mirror configure to provide the tracking output;
an imaging module disposed to receive the tracking output and the background output and provide a set of images based on the tracking output and background output wherein the imaging module comprises a composite imaging element, said composite imaging element configured to receive the background output and tracking output and provide a set of composite images, each image of said set of composite images including a background channel image and a tracking channel image wherein the background channel image and the tracking channel image are captured simultaneously; and
a processor module disposed to:
receive the set of images;
provide, based on the set of images, gaze tracking data; and
store, in a processor readable memory, the gaze tracking data.

4. A gaze tracking system comprising:
an optical module disposed to receive, from a target, illumination including an ambient light component and a controlled light component, and provide a background output and a tracking output, said background output consisting substantially of the ambient light component and said tracking output including the ambient light component and the controlled light component wherein the optical module comprises a first lens assembly configured to generate the background output, and a second lens assembly configured to generate the tracking output;
an imaging module disposed to receive the tracking output and the background output and provide a set of images based on the tracking output and background output wherein the imaging module comprises a composite imaging element, said composite imaging element configured to receive the background output and tracking output, and provide a set of composite images, each image of said set of composite images including a background channel image and a tracking channel image wherein the background channel image and the tracking channel image are captured simultaneously; and
a processor module disposed to:
receive the set of images;
provide, based on the set of images, gaze tracking data; and
store, in a processor readable memory, the gaze tracking data.

5. A method of gaze tracking comprising the steps of:
receiving from a target, illumination including an ambient light component and a controlled light component;
providing, based on the received illumination, a background output and a tracking output, said background output consisting substantially of the ambient light component and said tracking output including the ambient light component and the controlled light component;
receiving, at an imaging module, the tracking output and the background output wherein the set of images provided by the imaging module include a set of background channel images based on the background output and a set of tracking channel images based on the tracking output and wherein a plurality of images of the set of background channel images and a corresponding plurality of images of the set of tracking channel images are captured simultaneously;
providing, to a processor module, a set of images based on the tracking output and background output;
generating, at the processor module, gaze tracking data; and
storing, in a processor readable memory, the gaze tracking data.

6. A method of gaze tracking comprising the steps of:
receiving from a target, illumination including an ambient light component and a controlled light component;
providing, based on the received illumination, a background output and a tracking output, said background output consisting substantially of the ambient light component and said tracking output including the ambient light component and the controlled light component;
receiving, at an imaging module, the tracking output and the background output wherein the set of images provided by the imaging module comprises a set of composite images, each composite image of the set of composite images including a background channel image and a tracking channel image wherein the tracking channel image and background channel image are captured simultaneously;
providing, to a processor module, a set of images based on the tracking output and background output;
generating, at the processor module, gaze tracking data; and
storing, in a processor readable memory, the gaze tracking data.

7. A method of gaze tracking comprising the steps of:
receiving from a target, illumination including an ambient light component and a controlled light component;

providing, based on the received illumination, a background output and a tracking output, said background output consisting substantially of the ambient light component and said tracking output including the ambient light component and the controlled light component;

receiving, at an imaging module, the tracking output and the background output;

providing, to a processor module, a set of images based on the tracking output and background output wherein the set of images comprises a set of composite images, each image of said set of composite images including a background channel image and a tracking channel image wherein the background channel image and the tracking channel image are captured simultaneously;

generating, at the processor module, gaze tracking data; and storing, in a processor readable memory, the gaze tracking data.

* * * * *